(12) United States Patent
Young

(10) Patent No.: US 8,852,194 B2
(45) Date of Patent: Oct. 7, 2014

(54) REMOVAL OF PROSTHESES

(75) Inventor: Michael John Radley Young, Ashburton (GB)

(73) Assignee: Orthosonics Limited (GB)

( * ) Notice: Subject to any disclaimer, the term of this patent is extended or adjusted under 35 U.S.C. 154(b) by 838 days.

(21) Appl. No.: 12/525,617

(22) PCT Filed: Feb. 19, 2008

(86) PCT No.: PCT/GB2008/000588
§ 371 (c)(1),
(2), (4) Date: Aug. 3, 2009

(87) PCT Pub. No.: WO2008/102135
PCT Pub. Date: Aug. 28, 2008

(65) Prior Publication Data
US 2010/0100139 A1 Apr. 22, 2010

(30) Foreign Application Priority Data
Feb. 20, 2007 (GB) .................. 0703249.3

(51) Int. Cl.
*A61B 17/56* (2006.01)
*A61F 2/46* (2006.01)
*A61B 17/88* (2006.01)

(52) U.S. Cl.
CPC ....... *A61F 2/4603* (2013.01); *A61F 2002/4619* (2013.01); *A61B 17/8847* (2013.01); *A61F 2002/4683* (2013.01)
USPC ...................................... 606/86 A

(58) Field of Classification Search
USPC .......................... 606/86 A, 99, 104
See application file for complete search history.

(56) References Cited

U.S. PATENT DOCUMENTS

| | | | | |
|---|---|---|---|---|
| 5,300,021 A | * | 4/1994 | Wuchinich | 604/22 |
| 5,324,297 A | * | 6/1994 | Hood et al. | 606/99 |
| 5,330,481 A | * | 7/1994 | Hood et al. | 606/99 |
| 5,456,686 A | * | 10/1995 | Klapper et al. | 606/99 |
| 5,749,877 A | * | 5/1998 | Young | 606/99 |

(Continued)

FOREIGN PATENT DOCUMENTS

| | | |
|---|---|---|
| EP | 0617935 | 10/1994 |
| FR | 2749501 | 12/1997 |

(Continued)

OTHER PUBLICATIONS

Patents Act 1977—Examination Report Under Section 18(3) for Appln. No. GB 0803077.7, dated Feb. 2, 2011.

(Continued)

*Primary Examiner* — Christopher Beccia
(74) *Attorney, Agent, or Firm* — Carter, DeLuca, Farrell & Schmidt, LLP

(57) ABSTRACT

An apparatus to aid removal of a prosthetic implant cemented into bone that has an adapter to engage a proximal end of the implant, a clamp screw to hold the engaged end to the adapter in good acoustic contact, a generator for torsional or longitudinal mode ultrasonic vibrations and a coupling link to transmit the ultrasonic vibrations to the adapter and thence to the implant, the proximal end of the implant being gripped between a conical tip of the clamp screw and a raised portion of the adapter to avoid damping flexural mode oscillations induced in the implant by making the zone of contact between the adaptor and implant as narrow as possible.

23 Claims, 7 Drawing Sheets

(56) References Cited

U.S. PATENT DOCUMENTS

| | | | |
|---|---|---|---|
| 6,932,308 B2 * | 8/2005 | Talish et al. | 248/226.11 |
| 2006/0100548 A1 * | 5/2006 | Ferguson | 601/2 |
| 2007/0270833 A1 * | 11/2007 | Bonutti et al. | 606/61 |
| 2009/0024161 A1 * | 1/2009 | Bonutti et al. | 606/213 |
| 2010/0100138 A1 * | 4/2010 | Reynolds et al. | 606/86 A |

FOREIGN PATENT DOCUMENTS

| | | |
|---|---|---|
| GB | 2277448 | 11/1994 |
| GB | 2288120 | 10/1995 |
| WO | WO 91/11965 | 8/1991 |
| WO | WO 92/22259 | 12/1992 |
| WO | WO 2006/020803 | 2/2006 |
| WO | WO 2006/052498 | 5/2006 |

OTHER PUBLICATIONS

PCT International Search Report dated May 28, 2008 for PCT/GB2008/000588.

* cited by examiner

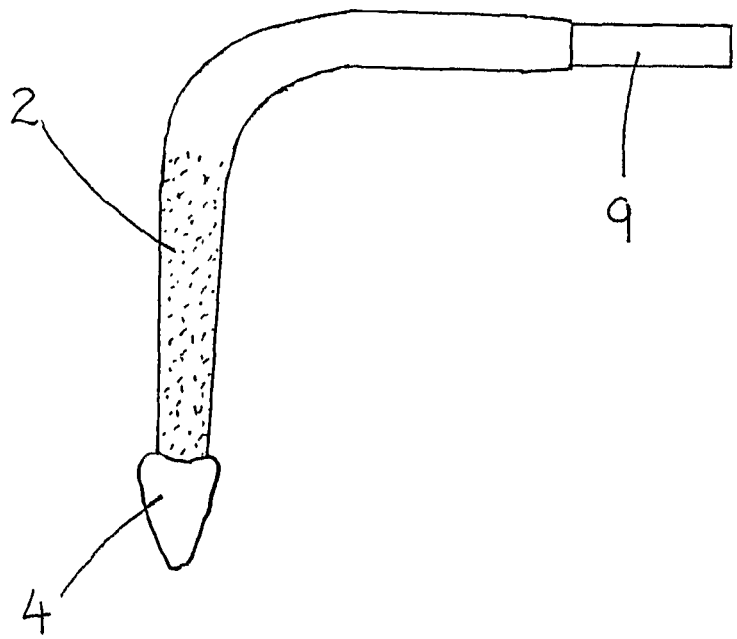
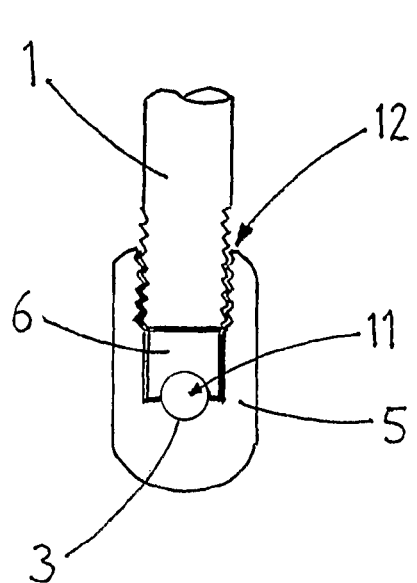
Fig 1
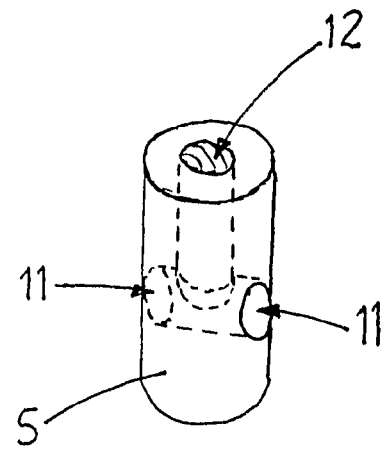
Fig 2
Fig 3

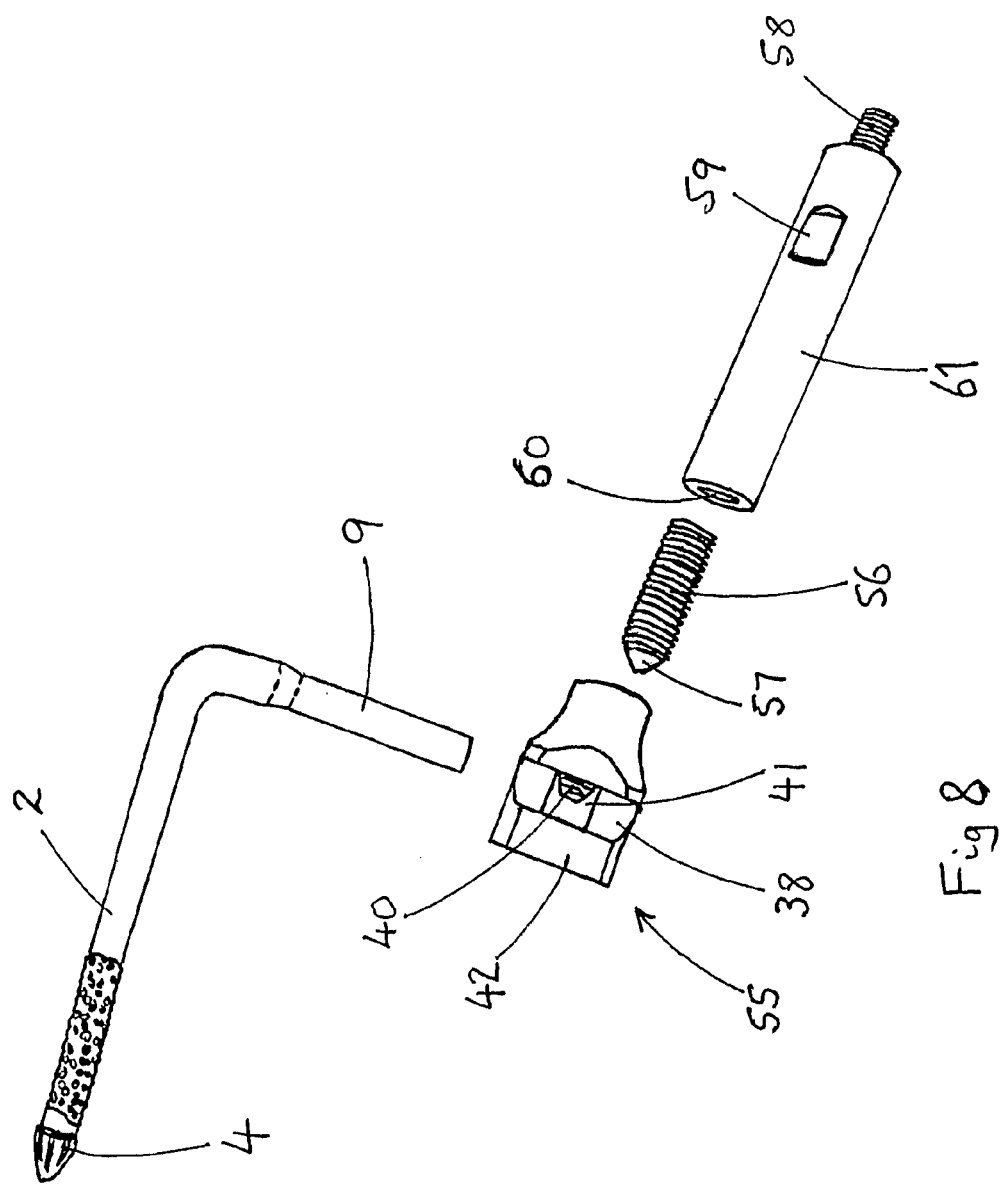

REMOVAL OF PROSTHESES

The present invention relates to a method and apparatus for removing prostheses when revising a surgical implant, particularly a spinal implant. More particularly, but not exclusively, it relates to an ultrasonically vibratable device for attachment to a prosthesis to generate vibrations in the prosthesis so as to free a remote end thereof from its embedment in bone material, such as that of a vertebra.

It is known to provide a spinal fusion system which allows mobility between adjacent vertebrae when they have been connected with the system. Adjacent vertebrae are connected together and spaced apart by one or more fusion implant members. Each implant member has a bent or straight tapered stem with a roughened surface conducive to strong bonding with orthopaedic bone cement which is used to hold the implant in place in a socket drilled into the bone.

In order to revise spinal fusions implanted in this way, the cement interface must be loosened to permit implant removal. The preferred method of achieving this is by the introduction of ultrasound into the cement to soften it, permitting the implant to be pulled free of the bony socket. This obviates the risk of damage to the bone that is attendant on other loosening methods.

It is hence an object of the present invention to provide apparatus and a method for removal of a surgical implant from bone that is more rapid, effective, reliable and/or safe than existing apparatus and methods.

According to a first aspect of the present invention there is provided apparatus to aid removal of a prosthetic implant from bone, said apparatus comprising adapter means to engage a proximal end of the implant, clamp means to hold said engaged end to the adapter means, means to generate ultrasonic vibrations and means to transmit said vibrations to the adapter means and thence to the implant.

In a preferred embodiment, the apparatus is adapted to aid removal of an implant from a spinal vertebra.

Preferably, the apparatus comprises means to generate torsional mode ultrasonic vibrations.

Alternatively, the apparatus comprises means to generate longitudinal mode ultrasonic vibrations.

Preferably, the adapter means is so locatable on the proximal end of the implant that said vibrations induce flexural mode oscillations in an embedded portion of the implant.

Advantageously, the adapter means is mountable to said proximal end at a point spaced from a longitudinal axis of said embedded portion.

Preferably, the adapter means is provided with recess means adapted to receive said proximal end.

Advantageously, the recess means comprises slot means extending into a body of the adapter means.

Alternatively, the recess means comprises passage means extending through a body of the adapter.

Preferably, the adapter means is provided with bore means extending therethrough into the recess means, said bore means being adapted to receive the clamp means operably.

The bore means and the clamp means may be cooperably threaded.

The clamp means is preferably provided at a first end with tapered tip means adapted to engage the proximal end of the implant, optionally adapted to penetrate said proximal end.

The clamp means may be provided at a second end remote from the first with means, such as socket means, for tool means to engage therewith to turn the clamp means.

The transmitting means may be connectable to the second end of the clamp means, optionally by means of a threaded aperture in its distal end adapted to receive cooperably a threaded said second end.

Preferably, the recess means is provided with constriction means extending adjacent an opening of the bore means, optionally extending solely adjacent said opening.

Said constriction means may be disposed on a face of the recess means opposing said opening.

Said constriction means may be so located as to cooperate with clamp means extending through the bore means, so as to grip the proximal end of the implant therebetween.

Advantageously, only the clamp means and the constriction means may then contact the proximal end of the implant.

The implant is then gripped substantially at a single point.

The constriction means may be so configured as to receive the proximal end of the implant locatingly, prior to engagement of the clamp means therewith.

The clamp means may comprise a distal extremity of the transmitting means.

According to a second aspect of the present invention there is provided a method of removing a prosthetic implant cemented into bone, comprising the steps of providing an apparatus as described in the first aspect above, attaching adapter means thereof around a proximal end of the implant, inserting clamp means thereof into bore means of the adapter means so as to be in acoustic contact with the implant, and applying ultrasonic vibrational energy to the adapter and thence to the implant.

Preferably, the method comprises the step of inducing flexural mode oscillations in the implant.

Advantageously, the method comprises the step of attaching the adapter means to said proximal end at a point spaced from a longitudinal axis of said implant.

The method may comprise so attaching the adapter means to said proximal end that the proximal end is gripped substantially at a single point.

The ultrasonic energy may be applied at a tuned frequency, for example tuned to a frequency maximising transmission to the implant Embodiments of the present invention will now be more particularly described by way of example and with reference to the figures of the accompanying drawings, in which FIG. 1 is a plan view of a first, cephalad, spinal implant member;

FIG. 2 is a schematic cross-sectional view of a first adaptor for attachment to said cephalad implant member;

FIG. 3 shows said first adaptor in perspective;

FIG. 8 is a perspective view of a fourth adaptor, similar to the second adaptor, and an ultrasonic coupling link prior to attachment to a cephalad implant member;

Figure 4:
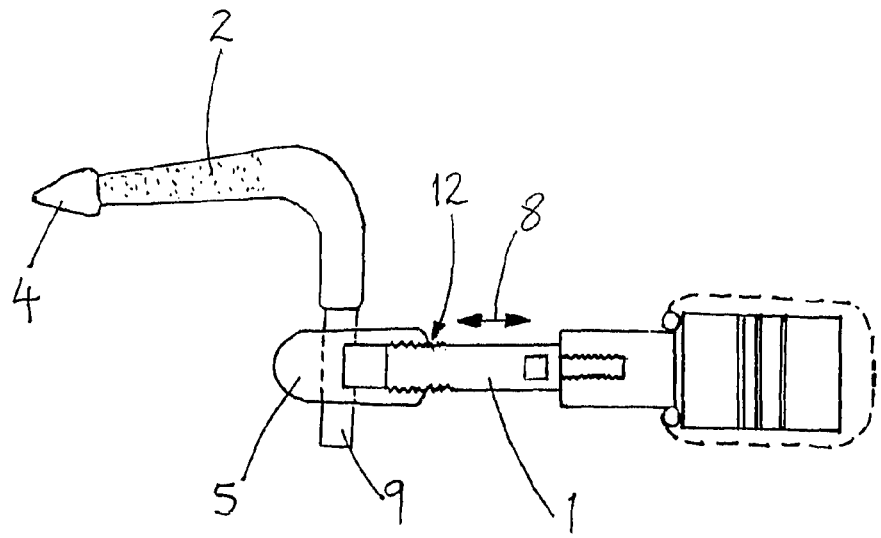
FIG. 4 shows, schematically, said first adaptor connected to a cephalad implant member and to an ultrasonic vibration device operable in longitudinal mode.

Referring now to the drawings, FIG. 1 shows a first cephalad spinal implant 2 in the form of a bent rod with a reduced cylindrical section 9 at a proximal first end and a distal spear shaped second end 4 for fixation into a vertebra. A portion of the elongate stem of the implant 2 adjacent the distal end 4 is roughened to aid cement bonding. In order to fix the implant 2 in place, a 10 mm poly(methylmethacrylate) cement bolus is created in cancellous bone to accommodate the distal end 4.

In order to loosen and extract the cephalad implant 2, an ultrasonic vibrator is linked to the implant via a tuned connecting link 1 mounted to a first acoustic adaptor 5. The adaptor 5 has an end access aperture 12 into which a cylindrical clamp element 6 slides, said clamp having a transverse part-cylindrical groove at its inner end, which forms, together with a part-cylindrical groove at the base of the access aperture 12, an enclosed cylindrical channel 11. The diameter of the channel 11 may be set to create an interference fit when placed around the reduced cylindrical section 9 of an implant 2. It is held in place by pressure from the coupling link 1, a distant end of which is threaded to engage with an internal thread of the access aperture 12.

Figure 5:
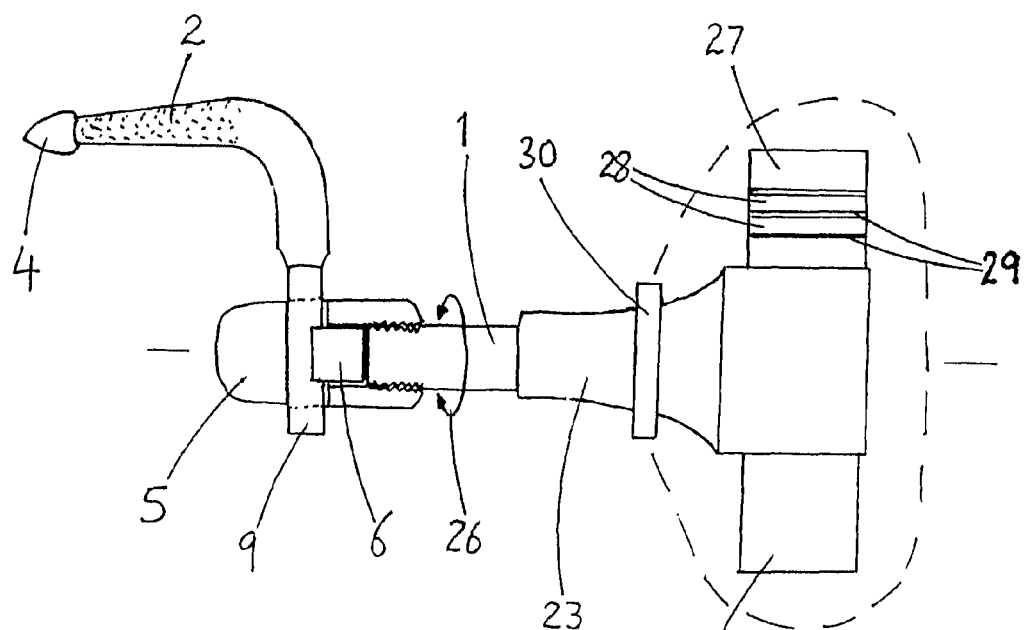
FIG. 5 shows, schematically, said first adaptor connected to a cephalad implant member and to an ultrasonic vibration device operable in torsional mode.

FIGS. 4 and 5 illustrate two alternative methods and apparatus designed to achieve softening of the cement volume in contact with the prosthetic implant.

FIG. 4 shows a view of the complete system, with transducer and adaptor in place. The distal end of the coupling link 1 is tightened in the threaded access aperture 12 in the adaptor 5 in order to clamp the adaptor 5 to the prosthetic implant 2, ensuring good acoustic coupling. The ultrasound system illustrated operates in a longitudinal mode, as indicated by arrows 8, and induces complex transverse vibrations in the prosthetic implant. The amplitude is adjusted until sufficient energy has been delivered to soften the cement around the distal end 4 and loosen the prosthetic implant 2.

An alternative oscillatory system is illustrated in FIG. 5 where a torsional mode ultrasonic transducer 23 generates rotational cyclic motion in coupling link 1, as indicated by arrows 26. Adaptor 5 couples torsional vibrations into the prosthetic stem generating a combination of torsional and flexural modes throughout the implant 2.

In this case, transducers 27 containing active PZT elements 28 and electrodes 29 are contained in a housing, illustrated schematically by the broken line, which attaches to a nodal flange 30 on a torsional horn 23.

FIGS. 6A to 7B show two preferred forms of adaptor which are even more effective than the first adaptor 5 shown above. The second adaptor 35 is intended for use with a cephalad implant, while the third adaptor 45 is intended for use with a caudal implant. Note: The spinal fusion system in question comprises two different forms of implant member, a pair of cephalad implant members and a pair of caudal implant members. The cephalad implants are implanted into the superior of the two vertebrae to be connected (cephalad indicating towards the skull) and the caudal implants are implanted into the inferior of the two vertebrae (caudal in human anatomy indicating towards the pelvis).

The elongate distal shaft 4 of each cephalad implant 2 is implanted into the superior vertebra, such that the proximal section 9 extends generally downwardly towards the inferior vertebra. The two proximal sections 9 are joined, in use, by a detachably mounted cross-bar (not shown) having a spherical bearing at each remote end.

Figure 10:
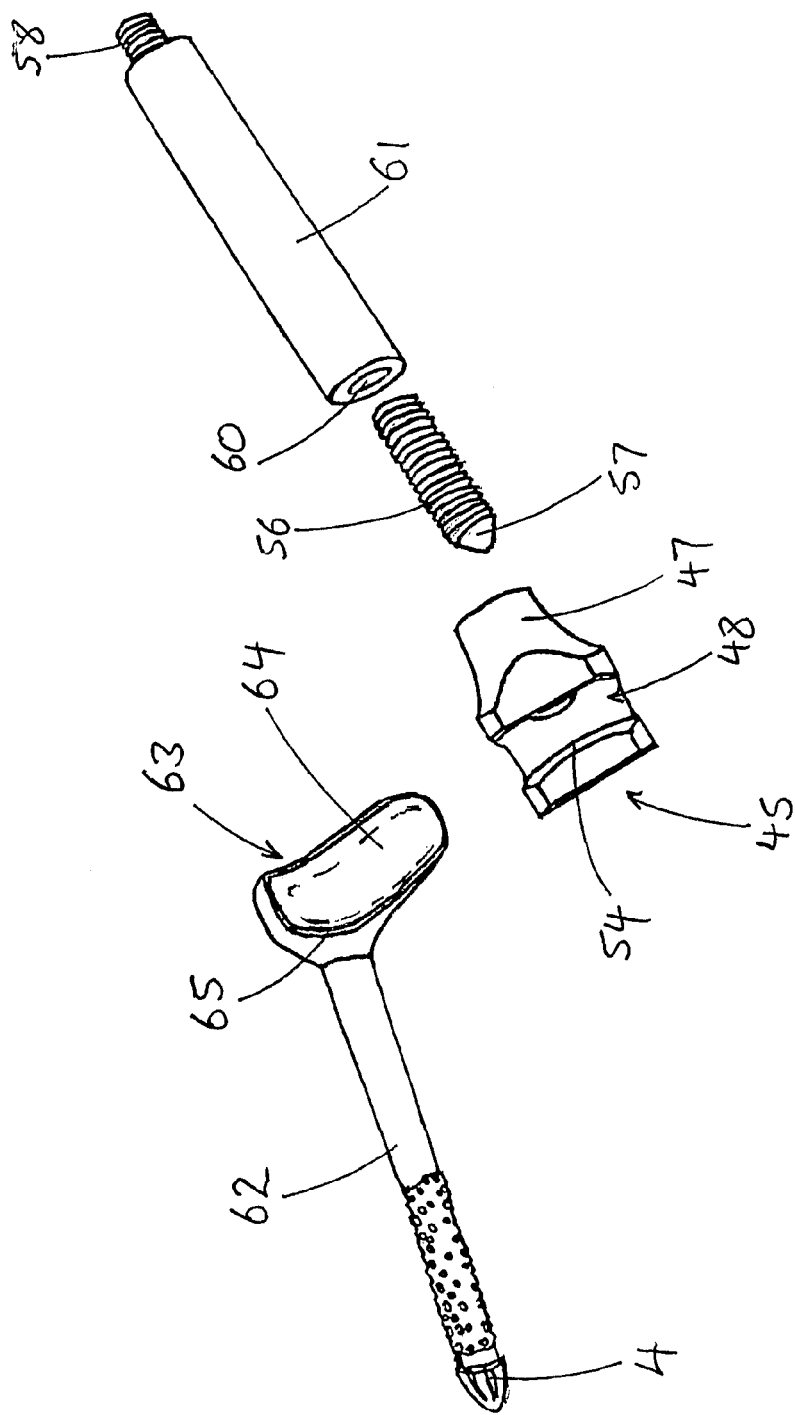
FIG. 10 is a perspective view of the third adaptor and a coupling link prior to attachment to a second, caudal implant member.
Figure 11:
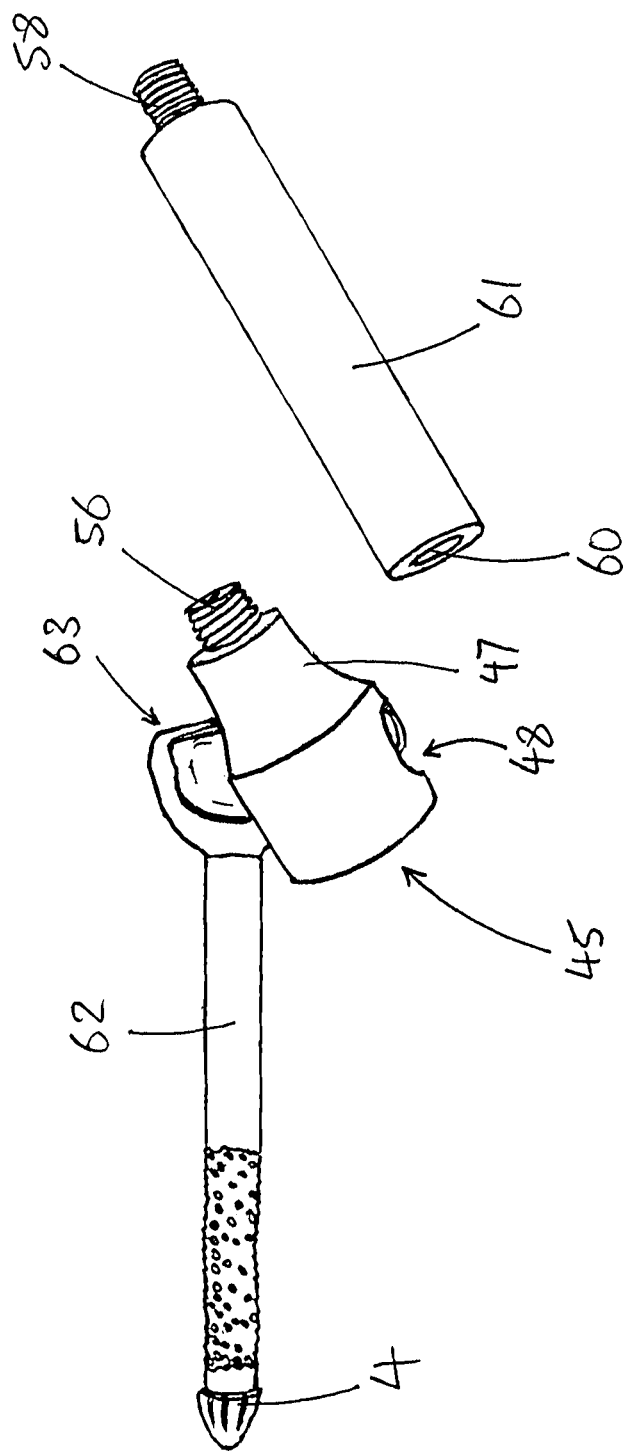
FIG. 11 is a perspective view of the third adaptor attached to the caudal implant member, prior to attachment of the link.

The caudal implants also comprise an elongate distal shaft 4, having a cup or scoop-shaped plate mounted to its proximal end (see FIGS. 10 and 11 for more details). The caudal implants are implanted into the inferior vertebra, such that the spherical bearings on the ends of the cross-bar are each received in a respective concave face of a cup plate.

This allows articulation of the vertebrae, while keeping their relative motion within limits, and reducing the load on weakened or damaged contact surfaces between the respective vertebrae.

Should this system require revision, the cross-bar and bearings may be removed, leaving a pair of cephalad implants and a pair of caudal implants to be removed. Since they differ greatly in shape, slightly different adaptors 35, 45 are required, but they demonstrate well the common features of the present invention, applicable to a range of different implants.

Figure 6A:
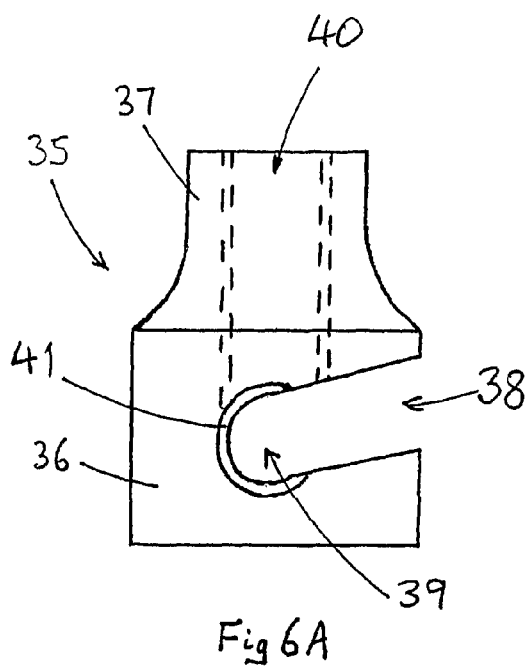
FIGS. 6A and 6B are a side elevation and a frontal elevation, respectively, of a second adaptor for attachment to a cephalad implant member.
Figure 6B:
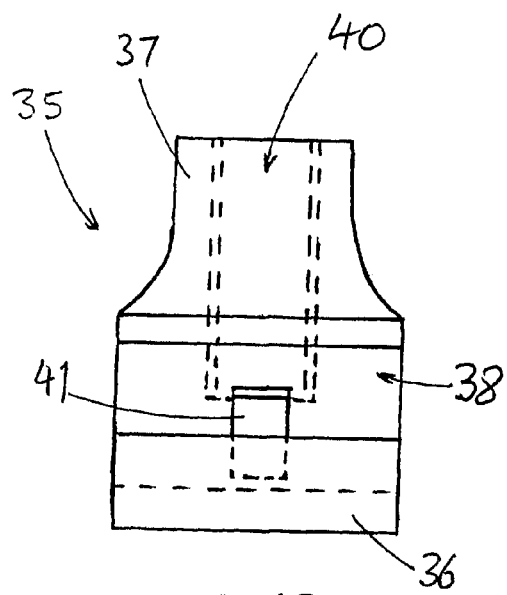

The second adaptor 35, shown in FIGS. 6A and 6B, comprises a cylindrical body 36, with a tapering neck 37 extending coaxially from the body 36. A slot 38 extends laterally into the body 36, angled slightly away from the neck 37, and terminating with a part-cylindrical inner end portion 39, generally aligned with a central axis of the body 36 and neck 37. A threaded bore 40 extends axially through the neck 37 and body 36, opening out into the part-cylindrical inner end 39 of the slot 38. A narrow cylindrical raised rim or ridge 41 extends circumferentially around an inside surface of the inner end 39, level with an axis of the threaded bore 40.

The slot 38 is dimensioned to receive the proximal section 9 of the cephalad implant 2; the angle makes it easier to slide over the proximal section 9 in situ. The narrow raised ridge 41 constricts the inner end 39 of the slot 38, such that it is locally close to an interference fit with the proximal section 9. To either side of the ridge 41, the inner end 39 is slightly larger in diameter, such that there is a gap between the proximal section 9 and the adaptor 35. (The) purpose of this is explained below).

Figure 7A:
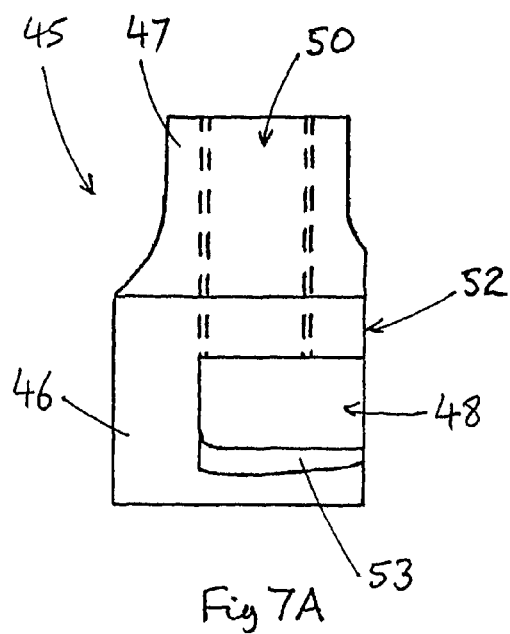
FIGS. 7A and 7B are a side elevation and frontal elevation, respectively, of a third adaptor for attachment to a caudal implant member.
Figure 7B:
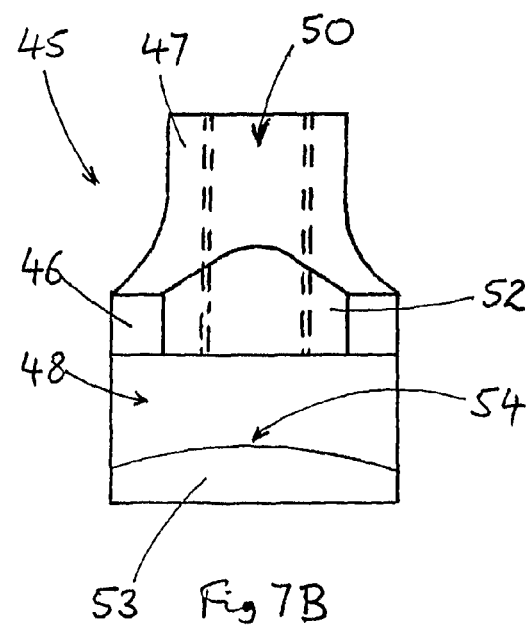

The third adaptor 45, shown in FIGS. 7A and 7B, comprises a substantially cylindrical body 46 with a tapering neck 47 extending coaxially therefrom. The body 46 and neck 47 are not quite cylindrically symmetrical, as a flat face 52 has been formed, parallel to their common axis, to make the adaptor 45 more compact and easier to manoeuvre in situ. A slot 48 extends perpendicularly into the body 46 from the flat face 52, terminating generally in alignment with the central axis of the body 46 and neck 47. A threaded bore 50 extends axially through the neck 47 and body 46, opening out into an inner end of the slot 48. A face 53 of the slot 48 opposite to the bore 50 is convexly curved, such that its apex 54 is aligned with an axis of the threaded bore 50.

The slot 48 is dimensioned to receive a plate of a caudal implant; the function and purpose of the convex face 53 is explained below with reference to FIGS. 10 and 11.

FIG. 8 shows a cephalad implant 2, a fourth adaptor 55 and a coupling link or waveguide 61, separated prior to attachment and use. The cephalad implant 2 is substantially identical to that shown in FIGS. 1, 4 and 5 above. The coupling link 61 is generally the same as the link 1 shown in FIGS. 2, 4 and 5, but differs slightly at its distal end where it is connected to the adaptor 55.

The fourth adaptor 55 is almost identical to the second adaptor 35 shown in FIGS. 6A and 6B, except that a flat face 42 has been formed, similar to that 52 of the third adaptor 45 shown in FIGS. 7A and 7B. The slot 38 to receive the proximal section 9 of the implant 2, the narrow ridge 41 and the threaded bore 40 (here visible where it opens into the slot 38) are identical.

The coupling link 61 is connectable to the adaptor 55 with a grub screw 56, which is dimensioned to engage with the threaded bore 40 of the adaptor 55. The grub screw 56 has a conical distal tip 57, optionally hardened. At its proximal end (not visible) it is provided with a socket configured to receive a screwdriver, or preferably an Allen (Registered Trade Mark) key or the like. At its distal end, the coupling link 61 is provided with a threaded axial bore 60, dimensioned to receive the proximal end of the grub screw 56. The coupling link 61 has a threaded stud 58 at its proximal end for connection to an ultrasound generator, such as those shown in FIGS. 4 and 5. A spanner flat 59 is provided to allow the coupling link 61 to be turned and tightened conveniently.

To attach the adaptor 55 to the implant 2, the proximal section 9 is introduced into the slot 38 and is located snugly at its inner end 39 by the narrow ridge 41. The grub screw 56 is introduced into the threaded bore 40 and turned until its conical distal tip 57 emerges into the slot 38 and contacts the proximal section 9 of the implant 2. The grub screw 56 is tightened until its tip 57 bites into the implant 2 to create a good acoustic contact and to secure it against the narrow ridge 41. Away from the ridge 41, the implant 2 does not contact the interior of the slot 38 or any other part of the adaptor 55.

The proximal end of the grub screw 56 remains proud of the neck 37 of the adaptor 55 at this stage. Once the adaptor 55 is securely attached to the implant 2, the threaded axial bore 60 of the link 61 is threaded onto the grub screw 56 until the coupling link 61 is securely butted up against the neck 37 of the adaptor 55, in good acoustic contact. (See FIG. 9 for the appearance of this assembly).

The ultrasound generator of choice, operating either in longitudinal or in torsional mode (not shown), is then mounted to the threaded stud 58.

To operate this apparatus, ultrasonic vibrations are generated at a tuned frequency and transmitted along the coupling link 61 into the adaptor 55, from which they are passed to the implant 2 via its contacts with the tip 57 of the grub screw 56 and the narrow ridge 41. Whether longitudinal or torsional mode, since these ultrasonic vibrations are imposed on the implant 2 off the longitudinal axis of the distal shaft 4, they induce flexural mode vibrations in the implant 2, and in the distal shaft 4 in particular. These flexural modes transfer vibrational energy from the distal shaft 4 into the cement encasing it, causing the cement to soften and weaken, and allowing the implant 2 to be withdrawn with relative ease after sufficient sonication.

The purpose of the narrow ridge 41 and the conical tip 57 of the grub screw 56 is to make the zone of contact between adaptor and implant as narrow as possible. A lengthy zone of contact, such as that present for the first adaptor 5 above, risks damping out many of the desired flexural modes along the implant. While the first adaptor 5 is reasonably effective (it still imposes off-axis vibrations to generate some flexural modes), the second 35 and fourth 55 adaptors are hence preferred.

FIG. 10 shows a caudal implant 62, a third adaptor 45 and a coupling link 61, separated prior to attachment and use. The coupling link 61 and associated grub screw 56 are identical to those shown in FIGS. 8 and 9 above, and the third adaptor 45 is substantially identical to that shown in FIGS. 7A and 7B.

The caudal implant 62 has a distal shaft 4 with a roughened portion to aid keying into the surrounding cement, very similar to that of the cephalad implant 2. However, at its proximal end it comprises a plate or cup 63 which extends laterally from the shaft 4. The plate 63 has a concave face 64 surrounded by a shallow rim 65, which in use retains the spherical bearing on the cross-bar of the assembled prosthesis, as described above. The concave face 64, being a bearing surface, is usually treated to harden it.

To attach the adaptor 45 to the implant 62, the adaptor 45 is fitted over one side of the plate 63 so that a large part of the plate 63 is received into the slot 48 (see FIG. 11). The grub screw 56 is passed down the threaded bore 50 of the adaptor 45 until its hardened conical nose 57 bites into the concave face 64 of the plate 63. This forms a good acoustic contact with the plate 63 and may also securely trap the adjacent rim 65 of the plate 63 between the nose 57 of the grub screw 58 and an inner wall of the slot 48. The reverse face of the plate 63 is also thus urged against the curved face 53 of the slot 48; since the apex 54 of the curved face 53 is aligned with the axis of the bore 50, the plate 63 will thus be gripped between the apex 54 and the conical nose 57 of the grub screw 58, and will not contact the interior of the slot 48 away from the apex 54.

FIG. 11 also illustrates how the proximal end of the grub screw 56 extends outwardly from the neck 47 of the adaptor 45, (as described above for the fourth adaptor 55) ready for the coupling link 61 to be attached thereto, again as described above.

Figure 9:
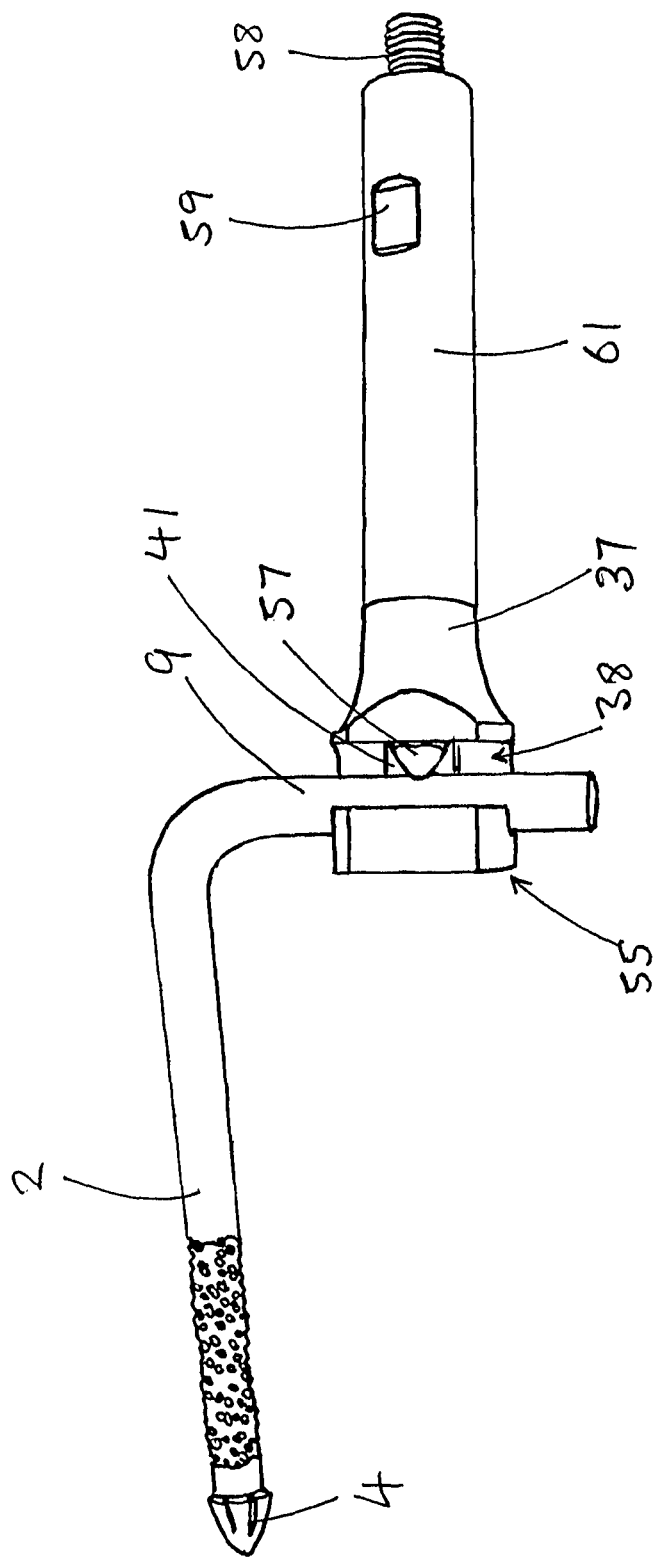
FIG. 9 is a perspective view of the fourth adaptor and the link attached to the cephalad implant member.

Once assembled and connected to an ultrasonic generator, this assembly operates very similarly to that shown in FIG. 9. Ultrasonic vibrations (torsional or longitudinal) at a frequency tuned to maximise transmission are transmitted along the coupling link 61 into the adaptor 45, and thence via the conical nose 57 of the grub screw 56 and the apex 54 of the curved face 53 into the plate 63. As above, these vibrations imposed off the longitudinal axis of the distal shaft 4 of the implant 62 induce flexural mode vibrations in the implant 62, and in particular in the distal shaft 4. These transfer vibrational energy into the cement around the shaft 4, which is progressively softened and loosened, allowing removal of the caudal implant 62.

The narrow contact zone between the adaptor 45 and the plate 63, formed by the nose 51 of the grub screw 56 and the apex 53, once again is sufficient to attach the adaptor 45 physically to the implant 62, while not damping out desirable flexural modes in the implant 62.

While the invention has been exemplified for cephalad and caudal implant members of a spinal fusion prosthesis, the approach described is believed to be applicable to the revision of a range of other implants cemented into bone.

The invention claimed is:

1. An apparatus configured to aid removal of a prosthetic implant from bone, the apparatus comprising:
    an adapter for engaging a proximal end of the implant,
    a clamp for holding said proximal end to the adapter,
    an ultrasonic vibrator for generating ultrasonic vibrations, and
    a transmitter for transmitting said vibrations to the adapter and thence to the implant;
    wherein the adapter is locatable on the proximal end of the implant and the proximal end of the implant interlocks with a distal end of the ultrasonic vibrator in a substantially T-shaped configuration within the adapter such that the ultrasonic vibrations induce flexural mode oscillations in the implant.

2. The apparatus as claimed in claim 1, adapted to aid removal of the implant from a spinal vertebra.

3. The apparatus as claimed in claim 1, wherein the adapter is mountable to said proximal end at a point spaced from a longitudinal axis of an embedded portion of the implant.

4. The apparatus as claimed in claim 1, wherein the adapter is provided with a recess for receiving said proximal end, said recess including a slot extending into a body of the adapter.

5. The apparatus as claimed in claim 4, wherein the adapter is provided with a bore extending through said adapter into the recess and being configured to operably receive the clamp.

6. The apparatus as claimed in claim 5, wherein the bore and the clamp are cooperably threaded.

7. The apparatus as claimed in claim 5, wherein the recess of the adapter is provided with a constriction extending adjacent an opening of the bore.

8. The apparatus as claimed in claim 7, wherein said constriction extends across a face of the recess opposing said opening.

9. The apparatus as claimed in claim 7, wherein said constriction is located so as to cooperate with the clamp extending through the bore, gripping the proximal end of the implant therebetween.

10. The apparatus as claimed in claim 7, wherein the constriction is configured to receive the proximal end of the implant locatingly, prior to engagement of the clamp therewith.

11. The apparatus as claimed in claim 1, adapted to grip the implant at a single point.

12. The apparatus as claimed in claim 1, wherein the clamp is provided at a first end with a tapered tip adapted to engage the proximal end of the implant.

13. A method for removing a prosthetic implant cemented into bone comprising the steps of:
providing an apparatus comprising:
an adapter engageable with a proximal end of the implant,
a clamp to hold said engaged end to the adapter,
an ultrasonic vibrator configured to generate ultrasonic vibrations, and
a transmitter configured to transmit said vibrations to the adapter and thence to the implant;
wherein the adapter is locatable on the proximal end of the implant and the proximal end of the implant interlocks with a distal end of the ultrasonic vibrator in a substantially T-shaped configuration within the adapter;
attaching the adapter around a proximal end of the implant;
inserting the clamp engagingly into the adapter so as to be in acoustic contact with the implant; and
applying ultrasonic vibrational energy to the adapter such that the ultrasonic vibrations induce flexural mode oscillations in the implant.

14. The method as claimed in claim 13, comprising the step of attaching the adapter to said proximal end at a point spaced from a longitudinal axis of an embedded portion of said implant.

15. The method as claimed in claim 13, comprising the step of so attaching the adapter to said proximal end that the proximal end is gripped at a single point.

16. An adaptor for connecting a proximal end of a prosthetic implant and an ultrasonic vibration generating device, the adaptor comprising:
a cylindrical body;
a neck extending coaxially from the body;
a slot extending laterally into the body, angled away from the neck, and terminating with a part-cylindrical inner end portion substantially aligned with a central axis of said body and neck;
a bore extending axially through said neck and opening out into said part-cylindrical inner end portion of said slot; and
a rim extending outwardly from and substantially circumferentially around an inside surface of said part-cylindrical inner end portion of said slot level with an axis of the bore;
wherein the adaptor is locatable on the proximal end of the implant and the proximal end of the implant interlocks with a distal end of the ultrasonic vibration generating device in a substantially T-shaped configuration within the adaptor such that the ultrasonic vibrations induce flexural mode oscillations in the implant.

17. The adaptor as claimed in claim 16, wherein a flat face is formed parallel to a common axis of said bore and neck.

18. An adaptor for connecting a proximal end of a prosthetic implant and an ultrasonic vibration generating device, the adaptor comprising:
a substantially cylindrical body;
a neck extending coaxially from said substantially cylindrical body, wherein a face is formed parallel to the common axis of said neck and substantially cylindrical body;
a slot extending perpendicularly into the body from the flat face terminating substantially in alignment with a central axis of said body and neck; and
a bore extending axially through said neck and body opening out into an inner end of said slot, wherein a face of said slot opposite to said bore has an apex aligned with an axis of said bore;
wherein the adaptor is locatable on the proximal end of the implant and the proximal end of the implant interlocks with a distal end of the ultrasonic vibration generating device in a substantially T-shaped configuration within the adaptor such that the ultrasonic vibrations induce flexural mode oscillations in the implant.

19. The adaptor as claimed in claim 18, wherein said neck is tapered.

20. The adaptor as claimed in claim 18, further comprising:
a coupling link connectable to said adaptor and ultrasonic vibration generating device via a screw, wherein said screw is engageable with said bore of said adaptor, and wherein said coupling link has an axial bore.

21. The adaptor as claimed in claim 20, wherein said screw has a conical distal tip.

22. The adaptor as claimed in claim 20, wherein said coupling link has a spanner flat.

23. The adaptor as claimed in claim 20, wherein said bore of said adaptor is threaded and said axial bore of said coupling link is threaded.

* * * * *